United States Patent [19]

Boswell, Jr. et al.

[11] 4,139,620
[45] Feb. 13, 1979

[54] 1-SUBSTITUTED-3-AMINOETHOXYPYR-ROLIDINES AND USE THEREOF

[75] Inventors: Robert F. Boswell, Jr.; Robert L. Duncan, Jr., both of Richmond, Va.

[73] Assignee: A. H. Robins Company, Inc., Richmond, Va.

[21] Appl. No.: 857,477

[22] Filed: Dec. 5, 1977

Related U.S. Application Data

[63] Continuation-in-part of Ser. No. 754,928, Dec. 28, 1976, Pat. No. 4,096,311.

[51] Int. Cl.$^2$ ................. C07D 413/12; A61K 31/535
[52] U.S. Cl. ................. 424/248.57; 544/129; 544/130; 544/141; 424/248.56
[58] Field of Search ............. 544/141, 130, 129; 424/248.54, 248.57

[56] References Cited

U.S. PATENT DOCUMENTS 3,984,436  10/1976  Jaeggi et al. ................. 544/141

Primary Examiner—Natalie Trousof
Assistant Examiner—R. W. Ramsuer

[57] ABSTRACT

1-Substituted-3-aminoethoxypyrrolidines having the formula

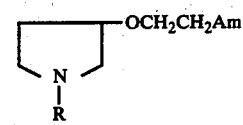

wherein R is benzyl, 2-ethoxyphenoxylower-alkyl, 2-propionyloxy-ethyl, 2-methoxy-4-acetylphenoxylower-alkyl, 4-fluorophenoxy lower alkyl, benzoyloxylower-alkyl, 3,4,5-trimethoxybenzoyloxylower-alkyl, 3,4,5-trimethoxybenzoyl, N-(4-methoxyphenyl) carbamoyl, 2-methoxyphenoxylower-alkyl, 3,4,5-trimethoxyphenyl-acetyl, 2-piperidinoethyl or carbamoyl, and Am is dilower-alkylamino, morpholino or piperidino having hypotensive properties are disclosed.

9 Claims, No Drawings

1-SUBSTITUTED-3-AMINOETHOXYPYRROLIDINES AND USE THEREOF

The present application is a continuation-in-part of copending application Ser. No. 754,928 filed Dec. 28, 1976, now U.S. Pat. No. 4,096,311.

FIELD OF INVENTION

The present invention relates to 3-aminoethoxypyrrolidines and more particularly to 1-substituted-3-aminoethoxypyrrolidines, pharmaceutically acceptable acid addition salts thereof and to methods of making and using them.

DESCRIPTION OF PRIOR ART

The prior art does not disclose any 1-substituted-3-($\omega$-aminoalkyl)pyrrolidines wherein the alkyl moiety is methylene, ethylene or propylene.

SUMMARY OF THE INVENTION

The compounds of the present invention may be broadly illustrated by the following structural formula:

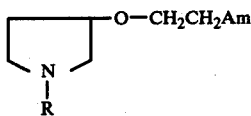

Formula I wherein;

R represents benzyl, 2-ethoxyphenoxylower-alkyl, 2-propionyloxyethyl, acetylphenoxylower-alkyl, 4-fluorophenoxylower-alkyl, benzoylozylower-alkyl, 3,4,5-trimethoxybenzoyloxylower-alkyl, 3,4,5-trimethoxybenzoyl, N-(4-methoxyphenyl)-carbamoyl, 2-methoxyphenoxylower-alkyl, 3,4,5-trimethoxyphenylacetyl, 2-piperidinoethyl, or carbamoyl, and Am is dilower-alkylamino, morpholino or piperidino.

The pharmaceutically acceptable acid addition salts of the free bases of Formula I are also included within the scope of the present invention.

The compounds of the invention are useful because of their pharmacological action on the central nervous system. The activity is demonstrable when the compounds are used in the form of the free base or in the form of their pharmaceutically acceptable acid addition salts. The preferred form of the compounds is as their pharmaceutically acceptable acid addition salts for increased water solubility and ease of administration.

DETAILED DESCRIPTION OF INVENTION

The 1-substituted-3-aminoethoxypyrrolidines of Formula I wherein R is other than benzyl are prepared by the following reaction scheme:

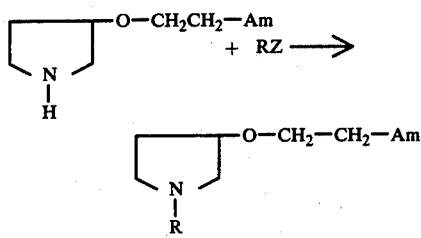

wherein R and Am are as defined hereinabove with the exception that R is not benzyl. Compounds of Formula I wherein R is benzyl are prepared as hereinafter noted by the reaction of 1-benzyl-3-pyrrolidinol with a 2-aminoethylchloride. The designation R—Z connotes nitrourea, an isocyanate or a compound having a reactive halide radical.

Generally speaking, the reaction of a 3-aminoethoxypyrrolidine II with nitrourea to give a 3-aminoethoxypyrrolidine-1-carboxamide I is run in a lower alkanol solvent, e.g., ethanol, usually at or below reflux temperature for a period of time of from about 4 hours to about 18 hours. The reaction of a 3-aminoethoxypyrrolidine II with an isocyanate to give an N-substituted-3-aminoethoxypyrrolidine-1-carboxamide I is run in a dry aprotic solvent such as benzene at room temperature for a period of time up to about 18 hours. The reaction of a 3-aminoethoxypyrrolidine II with a compound having an active halide radical is generally run in a solvent such as dimethylformamide or a lower alkanol at a temperature of from about 70°–90° C. in the presence of an inorganic acid acceptor such as sodium carbonate for a period of from about 8 to 18 hours. The products of Formula I are isolated by methods known to the art such as concentration of the reaction mixture under reduced pressure followed by crystallization of the product from a suitable solvent, distillation of the product in vacuo, or acid base extraction of the reaction mixture.

The 3-(2-aminoethoxy)pyrrolidine starting materials of Formula II are prepared by reacting a 1-benzyl-3-pyrrolidinol of Formula III with a 2-aminoethylchloride of Formula IV to give a 1-benzyl-3-(2-aminoethoxy)pyrrolidine of Formula I. The benzyl group is removed by hydrogenolysis using a palladium on charcoal catalyst (Pd/C). The reaction sequence is as follows:

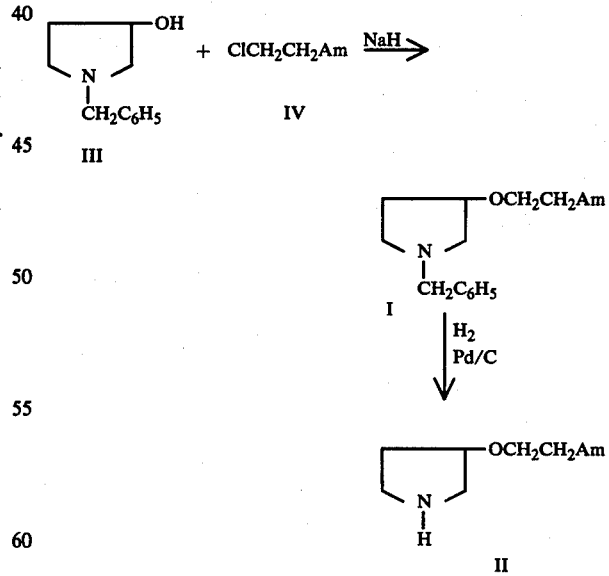

wherein Am is as defined hereinabove.

The hypotensive properties of the novel compounds of the present invention were determined using standard techniques with particular emphasis on the observation of the blood pressure of anesthetized dogs when the compounds were administered intravenously. The intensity and duration of the hypotensive effect was recorded using a Grass polygraph.

It is therefore an object of this invention to provide novel 1-substituted-3-aminoethoxypyrrolidines having utility as hypotensives. Another object is to provide methods for producing the novel compounds and methods for the utilization thereof. Other objects of this invention will be apparent to one skilled in the art and still other objects will become apparent hereinafter.

In the definition of symbols in the foregoing Formula I and where they appear elsewhere throughout this specification the terms have the following significance.

The term "lower-alkyl" as used herein includes straight and branched chain radicals of up to four carbon atoms inclusive and is exemplified by such groups as methyl, ethyl, propyl, isopropyl, butyl and tertiary butyl. "Lower-alkoxy" has the formula -O-lower-alkyl.

When halogen is referred to herein, preferably but not necessarily, a halogen of atomic weight less than eighty is employed.

The basic compounds of Formula I may be converted to and are most conveniently employed in the form of pharmaceutically acceptable acid addition salts. Such salts also have improved water solubility. The free base compounds of Formula I may be conveniently converted to their acid addition salts by reaction of the free base with the selected acid, preferably in the presence of an organic solvent inert to the reactants and reaction products under the conditions of the reaction. The acids which can be used to prepare the preferred non-toxic acid addition salts are those which produce, when combined with the free base, salts, the anions of which are relatively innocuous to the animal organism in therapeutic doses of the salts, so that beneficial physiological properties inherent in the free bases are not vitiated by side effects ascribable to the anions.

Appropriate acid addition salts are those derived from mineral acids such as hydrochloric acid, hydrobromic acid, hydriodic acid, nitric acid, sulfuric acid, and phosphoric acid; and organic acids such as maleic acid, oxalic acid, lactic acid, fumaric acid, and tartaric acid.

The acid addition salts are prepared either by dissolving the free base in an aqueous solution containing the appropriate acid and isolating the salt by evaporating the solution, or by reacting the free base and the selected acid in an organic solvent, in which case the salt ordinarily separated directly or can be conventionally recovered by concentration of the solution or the like. Conversely, the free base may be obtained conventionally by neutralizing the acid addition salt with an appropriate base such as ammonia, ammonium hydroxide, sodium carbonate or the like, extracting the liberated base with a suitable solvent, illustratively, ethyl acetate or benzene, drying the extract and evaporating to dryness or fractionally distilling or in other conventional manner.

The novel compounds of the present invention are more fully exemplified by the examples hereinafter described.

PREPARATION 1

3-(2-Dimethylaminoethoxy)pyrrolidine

A solution of 10.0 g. (0.0402 mole) of 1-benzyl-3-(2-dimethylaminoethoxy)pyrrolidine in ethanol containing 10% palladium on charcoal was shaken at 60° C. in about three atmospheres of hydrogen until the theoretical amount of hydrogen was used. The cooled filtered solution was concentrated at reduced pressure to give a quantitative yield of oily product. The structure was confirmed by its nuclear magnetic resonance spectrum.

PREPARATION 2

3-(2-Morpholinoethoxy)pyrrolidine

A solution of 30.8 g. (0.106 mole) of 1-benzyl-3-(2-morpholinoethoxy)pyrrolidine in 200 ml. of ethanol containing 10% palladium on charcoal was shaken at 60° C. in about three atmospheres of hydrogen until the theoretical amount of hydrogen was used. Concentration of the cooled filtered solution at reduced pressure gave a quantitative yield of oily product. The structure was confirmed by its nuclear magnetic resonance spectrum.

PREPARATION 3

3-(2-Piperidinoethoxy)pyrrolidine 3-(2-Piperidinoethoxy)pyrrolidine was prepared by debenzylation of 1-benzyl-3-(2-piperidinoethoxy)pyrrolidine according to Preparation 1.

EXAMPLE 1

1-Benzyl-3-(2-dimethylaminoethoxy)pyrrolidine Dioxalate

In a nitrogen atmosphere 36 g. (0.25 mole) of N,N-dimethylaminoethyl chloride hydrochloride was added in small portions to a stirring suspension of 21 g. (0.5 mole) of a 57% mineral oil dispersion of sodium hydride in 200 ml. of toluene. The reaction mixture was heated to about 50° C. A solution of 35.4 g. (0.2 mole) of 1-benzyl-3-pyrrolidinol in 50 ml. of toluene was added dropwise at a rate such as to control the evolution of hydrogen. After the addition was completed and the evolution of hydrogen ceased, the heat on the reaction mixture was increased. At about 80° C. a vigorous evolution of hydrogen began with considerable foaming. An ice water bath was used to control the temperature for a short time. After the evolution of hydrogen slowed to 1 to 2 bubbles per second, heat was reapplied and the reaction mixture was stirred and heated at about 90° C. overnight. The reaction mixture was cooled and water was added to slowly decompose any excess sodium hydride. The toluene layer was separated, washed with water, dried over anhydrous magnesium sulfate and filtered. Concentration of the filtrate at reduced pressure gave 47.1 g. of crude product (95%). The oil was dissolved in isopropyl ether and the dioxalate salt was prepared. Recrystallization from methanol-isopropyl ether gave 20.1 g. of off-white solid melting at 135°-137° C.

Analysis: Calculated for $C_{19}H_{28}N_2O_9$: C,53.27; H,6.59; N,6.54. Found: C,53.20; H,6.52; N,6.44.

EXAMPLE 2

1-Benzyl-3-(2-morpholinoethoxy)pyrrolidine Dioxalate

A solution of 39.5 g. (0.25 mole) of 1-benzyl-3-pyrrolidinol in 100 ml. of dry toluene was added dropwise to a stirring, refluxing suspension of 14.8 g. (0.35 mole) of a 57% suspension of sodium hydride in 250 ml. of dry toluene. The addition was completed at such a rate so as to control the evolution of gas. After the addition was complete, the reaction mixture was heated at reflux for an additional hour. The free base of 93 g. (0.5 mole) of β-chloroethylmorpholine hydrochloride was extracted into toluene. The toluene was washed with water and dried over anhydrous magnesium sulfate. After filtering, the filtrate was added dropwise to the refluxing reaction mixture. After the addition was complete (1.5 hr.) the reaction mixture was heated at reflux for 8 hrs. The reaction mixture was brought to room temperature and an excess of water was added. The organic layer was separated and washed with water, dried over anhydrous magnesium sulfate and filtered. The filtrate was concentrated under reduced pressure to give 73 g. of crude product. An acidbase extraction process removed mineral oil from the crude product. The crude product weighed 60.8 g. (83%). The material was distilled at 135°–140° C./0.02 mm. to give 35.3 g. of pure material. The dioxalate salt was prepared and recrystallization from methanol-isopropyl ether gave the product melting at 158.5°–160° C.

Analysis: Calculated for $C_{21}H_{28}N_2O_{10}$: C,53.84; H,6.02; N,5.98. Found: C,53.53; H,6.40; N,5.87.

EXAMPLE 3

1-Benzyl-3-(2-piperidinoethoxy)pyrrolidine Dioxalate

A solution of 42.5 g. (0.24 mole) of 1-benzyl-3-pyrrolidinol in 100 ml. of dry toluene was added slowly to a stirring refluxing suspension of 14.8 g. (0.35 mole) of a 57% mineral oil-sodium hydride dispersion in 250 ml. of dry toluene. The rate of addition was adjusted to give a gentle evolution of hydrogen. After the addition was complete the reaction mixture was heated at reflux another hour to ensure complete reaction. The free base from 100 g. (0.543 mole) of 1-β-chloroethylpiperidine hydrochloride was extracted into toluene from a basic aqueous solution. The toluene extract was washed with water, dried over magnesium sulfate, filtered and added dropwise to the above reaction mixture at reflux temperature. When this addition was complete, the reaction mixture stirred at reflux overnight. After cooling, excess water was carefully added. The toluene layer was separated, dried over magnesium sulfate, filtered and concentrated at reduced pressure to give 93.4 g. crude product. Impurities were distilled away under high vacuum distillation up to 125° C. The residue of 60 g. was the desired product (87% yield). Treatment of 5.0 g. of the product with 4.4 g. oxalic acid dihydrate gave 7.8 g. of the dioxalate salt; m.p. 144°–147° C. The salt was recrystallized from isopropanol-methanol to give 5.7 g. of off-white crystalline product; m.p. 150°–152° C.

Analysis: Calculated for $C_{22}H_{32}N_2O_9$: C,56.40; H,6.89; N,5.98. Found: C,56.27; H,6.81; N,6.01.

EXAMPLE 4

3-[2-(Dimethylamino)ethoxy]-1-[2-(o-ethoxyphenoxy)ethyl]pyrrolidine Dioxalate

A mixture of 4.0 g. (0.025 mole) of 3-(2-dimethylaminoethoxy)pyrrolidine, 6.6 g. (0.027 mole) of 2-(o-ethoxyphenoxy) ethyl bromide and 2.5 g. (0.03 mole) of sodium bicarbonate in 50 ml. of dry dimethylformamide was stirred at 93° C. for 18 hr. The cooled reaction mixture was diluted with about 500 ml. water and extracted with benzene. The benzene extracts were washed with water, dried over anhydrous magnesium sulfate and filtered. Concentration of the filtrate under reduced pressure gave 3.4 g. (42%) of crude product. The crude product was dissolved in isopropyl alcohol and the dioxalate salt was prepared. Recrystallization of the dioxalate salt from methanolisopropyl ether gave 4.6 g. of off-white solid melting at 140.5°–142° C.

Analysis: Calculated for $C_{22}H_{34}N_2O_{11}$: C, 52.58; H, 6.82; N, 5.58. Found: C, 52.48; H, 6.81; N, 5.56.

EXAMPLE 5

3-[2-(Dimethylamino)ethoxy]-1-(2-propionyloxy)ethylpyrrolidine Dioxalate

A mixture of 9.0 g. (0.05 mole) of 2-bromoethylpropionate, 8.0 g. (0.05 mole) of 3-(2-N,N-dimethylaminoethoxy)pyrrolidine and 8.5 g. (0.1 mole) of sodium bicarbonate in 250 ml. of dry dimethylformamide was stirred at 90° C. for 16 hr. After cooling, the reaction mixture was diluted to about 800 ml. with water, the aqueous mixture was extracted several times with chloroform and the combined chloroform extracts were washed with water and dried over anhydrous magnesium sulfate. The mixture was filtered and the filtrate was concentrated under reduced pressure. The residual crude oil was triturated in petroleum ether (30°–60° C.). The petroleum ether was decanted off and evaporated. The oil that remained was treated with oxalic acid to form the dioxalate salt. The salt was recrystallized from methanol-isopropyl ether to give 4.3 g. (10%), melting at 142°–143° C.

Analysis: Calculated for $C_{17}H_{30}N_2O_{11}$: C, 46.57; H, 6.90; N, 6.39. Found: C, 46.57; H, 6.91; N, 6.35.

EXAMPLE 6

3-(2-Dimethylaminoethoxy)-1-[3-(4-acetyl-2-methoxyphenoxy) propyl]pyrrolidine Dioxalate A mixture of 6.9 g. (0.029 mole) of 3-(p-acetyl-o-methoxyphenoxy)propyl chloride, 5 g. (0.032 mole) of 3-[2-(dimethylamino)-ethoxy]pyrrolidine and 3.4 g. (0.04 mole) of sodium bicarbonate in 100 ml. of dry dimethylformamide was heated at 95° C. overnight. The mixture was cooled, an excess of water was added and the aqueous mixture was extracted with chloroform. The chloroform extracts were dried over anhydrous magnesium sulfate, filtered and the filtrate was concentrated under reduced pressure to give 8.2 g. (79%) of crude product. The dioxalate salt was prepared using isopropyl alcohol and oxalic acid dihydrate. The salt was recrystallized from ethanol-isopropanol to give 6.4 g., melting at 126°–128° C.

Analysis: Calculated for $C_{24}H_{36}N_2O_{12}$: C, 52.94; H, 6.66; N, 5.14. Found: C, 52.72; H, 6.56; N, 4.97.

EXAMPLE 7

3-[2-(Dimethylamino)ethoxy]-1-(2-benzoyloxy)ethylpyrrolidine Dioxalate

A mixture of 2-bromoethyl benzoate (5.8 g., 0.025 mole), 3.4 g. (0.0215 mole) of 3-(2-dimethylaminoethoxy)pyrrolidine and 2.1 g. (0.05 mole) of sodium bicarbonate in 100 ml. of dry dimethylformamide was heated at 90° C. for 16 hr. The reaction mixture was cooled, diluted to about 500 ml. with water and the aqueous solution was extracted with chloroform. The combined extracts were washed with water and dried over anhydrous magnesium sulfate. The mixture was filtered and the filtrate was concentrated under reduced pressure to give 4.0 g. (52%) of crude product. The dioxalate salt was prepared to give 3.0 g. melting at 165°–166° C. after recrystallization from methanol-isopropyl ether.

Analysis: Calculated for $C_{21}H_{30}N_2O_{11}$: C, 51.85; H, 6.22; N, 5.76. Found: C, 51.81; H, 6.23; N, 5.80.

EXAMPLE 8

3-[2-(Dimethylamino)ethoxy]-1-[3-(3,4,5-trimethoxybenzoyloxy)ethyl]pyrrolidine dioxalate A mixture of 5.4 g. (0.017 mole) of 2-bromoethyl-3,4,5-trimethoxybenzoate, 2.7 g. (0.017 mole) of 3-(2-dimethylaminoethoxy)pyrrolidine and 2.7 g. (0.032 mole) of sodium bicarbonate in 100 ml. of dry dimethylformamide was heated at 90° C. for 16 hr. After cooling, the reaction mixture was diluted to about 700 ml. with water and the aqueous mixture was extracted several times with chloroform. The combined chloroform extracts were washed with water and dried over anhydrous magnesium sulfate. The mixture was filtered and the filtrate was concentrated under reduced pressure to give 5.0 g. (73%) of crude product. The oxalate salt was prepared and yielded 3.0 g. of salt after recrystallization from methanol-isopropyl ether. The salt melted at 141°–142° C.

Analysis: Calculated for $C_{24}H_{36}N_2O_{14}$: C, 50.00; H, 6.29; N, 4.86. Found: C, 49.69; H, 6.21; N, 4.76.

EXAMPLE 9

1-Benzyl-3-(2-dimethylaminoethoxy)pyrrolidine Bismethobromide

A stirred solution of 7.2 g. (0.08 mole) of methylbromide in 100 ml. of methyl ethyl ketone in an ice-ethanol bath was treated with 6.2 g. (0.04 mole) of 1-benzyl-3-dimethylaminoethoxy pyrrolidine. The product separated as a gum. Several attempts to recrystallize the gummy product resulted in only a semisolid residue. The product was cleaned by trituration in a combination of solvents to the point that the nuclear magnetic resonance spectrum and elemental analysis were good. The product obtained weighed 6.0 g. (34.2%).

Analysis: Calculated for $C_{17}H_{30}Br_2N_2O$: C, 46.59; H, 6.90; N, 6.39. Found: C, 46.72; H, 7.65; N, 6.61.

EXAMPLE 10

3-(2-Dimethylaminoethoxy)-1-(3,4,5-trimethoxybenzoyl)pyrrolidine Hydrochloride Dihydrate A solution of 3.9 g. (0.017 mole) of 3,4,5-trimethoxybenzoyl chloride in 20 ml. of dry benzene was added dropwise to a stirring solution of 2.0 g. (0.0126 mole) of 3-(2-dimethylaminoethoxy) pyrrolidine and 1.4 g. (0.014 mole) of triethylamine in 30 ml. of dry benzene. After the addition was complete, the reaction mixture was stirred for one hour and then another gram of the acid chloride in 10 ml. of dry benzene and 1 g. of the triethylamine were added to the reaction mixture. The mixture was warmed to about 50° C. for 1 hr., cooled and filtered. The filtrate was concentrated under reduced pressure and the residual oil was triturated in ether. The triturated mixture was filtered and the filtrate was concentrated to give 1.5 g. (33.8%) of product. The oily product was dissolved in ether and the hydrochloride salt was prepared. The hydrated hydrochloride salt melted at 96°–102° C.

Analysis: Calculated for $C_{18}H_{33}ClN_2O_7$: C, 50.88; H, 7.83; N, 6.59. Found: C, 51.44; H, 7.52; N, 6.50.

EXAMPLE 11

3-(2-Dimethylaminoethoxy)-4'-methoxy-1-pyrrolidinecarboxanilide

A solution of 3.0 g. (0.02 mole) of p-methoxyphenyl isocyanate in 10 ml. of dry benzene was added dropwise to a stirring solution of 3.2 g. (0.02 mole) of 3-(2-dimethylaminoethoxy)pyrrolidine in 100 ml. of dry benzene under anhydrous conditions. When the addition was complete, the reaction mixture was allowed to stir for two hours. The mixture was concentrated under reduced pressure to give 4.9 g. (80%) of product which crystallized upon standing. Recrystallization from benzeneisooctane gave 4.8 g. of solid melting at 92°–94° C.

Analysis: Calculated for $C_{16}H_{25}N_3O_3$: C, 62.52; H, 8.20; N, 13.67. Found: C, 62.30; H, 8.19; N, 13.80.

EXAMPLE 12

1-[4-(4-Fluorophenoxy)butyl]-3-(2-morpholinoethoxy) pyrrolidine Dioxalate

A mixture of 4-(p-fluorophenoxy)butyl bromide (3.5 g., 0.0152 mole), 3-[2-(4-morpholino)ethoxy]pyrrolidine (3.0 g., 0.015 mole), and sodium bicarbonate (2.5 g., 0.3 mole) in 50 ml. of dry dimethylformamide was stirred for 16 hr. at 85°–90° C. The solvent was removed at reduced pressure by a rotary evaporator and the residue dissolved in chloroform. The chloroform solution was washed with water, dried over anhydrous magnesium sulfate, filtered and concentrated at reduced pressure to give 5.3 g. crude product (95.5% yield). The oil was dissolved in methanol and treated with 3.7 g. oxalic acid dihydrate to give 5.9 g. of the dioxalate salt, m.p. 165°–168° C. The salt was recrystallized from methanol-isopropyl ether to give 5.3 g. salt, m.p. 171°–173° C.

Analysis: Calculated for $C_{24}H_{35}FN_2O_{11}$: C, 52.74; H, 6.46; N, 5.13. Found: C, 52.78; H, 6.54; N, 5.06.

EXAMPLE 13

1-[3-(2-Methoxyphenoxy)propyl]-3-(2-morpholinoethoxy) pyrrolidine Dioxalate

A mixture of 3.0 g. (0.15 mole) of 3-[2-(4-morpholino)ethoxy]pyrrolidine, 3.6 g. (0.152 mole) of 3-(o-methoxyphenoxy) propyl bromide and 2.5 g. (0.03 mole) of sodium bicarbonate was stirred in 50 ml. of dry dimethylformamide for 16 hours at 85°–90° C. After cooling, the reaction mixture was diluted to about 400 ml. volume with water and extracted three times with 100 ml. portions of chloroform. The combined extract was washed with water, dried over anhydrous magnesium sulfate, filtered and concentrated at reduced pressure to give 4.6 g. crude oily product (83% yield). The oil was dissolved in a small amount of methanol and added to a solution of 3.2 g. oxalic acid dihydrate in about 100 ml. of a mixture of equal parts of methanol-isopropyl ether to form the dioxalate salt (obtained 6.2 g., m.p. 162°–163° C.). This was recrystallized from methanol to give 3.8 g. product, m.p. 162.5°–165° C.

Analysis: Calculated for $C_{24}H_{36}N_2O_{12}$: C, 52.94; H, 6.66; N, 5.14. Found: C, 52.73; H, 6.58; N, 5.07.

EXAMPLE 14

3-(2-Morpholinoethoxy)-1-[2-(3,4,5-trimethoxybenzoyloxy)ethyl]pyrrolidine Dioxalate A mixture of 3.0 g. (0.015 mole) of 3-[2-(4-morpholino) ethoxy]pyrrolidine, 4.8 g. (0.015 mole) of 2-bromoethyl-3,4,5-trimethoxybenzoate and 2.5 g. (0.03 mole) of sodium bicarbonate was stirred in 50 ml. dry dimethylformamide for 16 hours at 85°–90° C. After cooling, the reaction mixture was diluted with 350 ml. water and extracted three times with 100 ml. portions of chloroform. The combined extract was washed with water, dried over anhydrous magnesium sulfate, filtered and concentrated at reduced pressure to give 5.4 g.

crude oily product (83% yield). The crude oil was dissolved in a small amount of methanol and treated with a methanol-isopropyl ether solution of 3.2 g. oxalic acid dihydrate to give 7.4 g. dioxalate salt, m.p. 180.5°–182° C. The salt was recrystallized from methanol to give 4.5 g. product, m.p. 184°–185.5° C.

Analysis: Calculated for $C_{26}H_{38}N_2O_{15}$: C, 50.48; H, 6.19; N, 4.53. Found: C, 50.42; H, 6.21; N, 4.47.

EXAMPLE 15

N-(4-Methoxyphenyl)-3-(2-morpholinoethoxy)-1-pyrrolidinecarboxamide

Under anhydrous conditions 2.2 g. p-methoxyphenyl isocyanate in 10 ml. of reagent grade benzene was added dropwise to a stirring solution of 3.0 g. (0.15 mole) of 3-(2-morpholinoethoxy) pyrrolidine in 40 ml. of reagent grade benzene. After the addition was complete the reaction mixture was stirred overnight at room temperature and then concentrated at reduced pressure to give the theoretical yield of crude product, which would not crystallize nor form addition salts. The crude product was chromatographed on a column of magnesium silicate to give 1.4 g. of oily product. The nuclear magnetic resonance spectrum and mass spectrum analysis agreed with the proposed structure.

Analysis: Calculated for $C_{18}H_{27}N_3O_4$: C, 61.87; H, 7.79; N, 12.03. Found: C, 61.12; H, 7.80; N, 11.87.

EXAMPLE 16

3-(2-Morpholinoethoxy)-1-(3,4,5-trimethoxyphenylacetyl) pyrrolidine Hemihydrate

Under anhydrous conditions 5.3 g. crude 3,4,5-trimethoxyphenylacetic acid chloride [equivalent to 4.5 g. (0.0184 mole) by nuclear resonance spectrum analysis] in 20 ml. dry benzene was added dropwise to a stirring mixture of 3.7 g. (0.0184 mole) of 3-(2-morpholinoethoxy)pyrrolidine and 30 g. (0.0217 mole) of potassium carbonate in 50 ml. dry benzene. The product formed rapidly and separated out as a gummy mass. After stirring 1 hr. at room temperature, chloroform was stirred into the reaction mixture to dissolve the product. The inorganic materials were removed by filtration and the filtrate concentrated at reduced pressure to give 5.3 g. crude product (70% yield). A portion (2.6 g.) of the crude product was chromatographed on magnesium silicate to give 1.6 g. of pure product.

Analysis: Calculated for $C_{42}H_{66}N_4O_{13}$: C, 60.41; H, 7.97; N, 6.71. Found: C, 60.34; H, 7.89; N, 6.61.

EXAMPLE 17

1-(2-Piperidinoethyl)-3-(2-piperidinoethoxy)pyrrolidine Trioxalate

A solution of 10.0 g. (0.051 mole) of 3-(2-piperidinoethoxy) pyrrolidine and 10.4 g. (0.07 mole) of 1-(2-chloroethyl)piperidine in 200 ml. dry benzene was stirred with 28 g. (0.2 mole) of potassium carbonate at reflux for 15 hr. After cooling, the reaction mixture was filtered and concentrated. The residual oil was molecularly distilled to give a slightly impure product which when treated with three equivalents of oxalic acid dihydrate gave 9.3 g. of the trioxalate salt, m.p. 155°–162° C. (32% yield). The salt was recrystallized from methanol to give 5.8 g. of white crystalline salt, m.p. 177°–179° C.

Analysis: Calculated for $C_{18}H_{35}N_3O \cdot 3\ C_2H_2O_4$: C, 49.74; H, 7.13; N, 7.25. Found: C, 49.50; H, 7.00; N, 7.03.

EXAMPLE 18

3-(2-Piperidinoethoxy)-1-pyrrolidinecarboxamide

Nitrourea (7.3 g., 0.055 mole of 80% wet reagent) and 3-(2-piperidinoethoxy)pyrrolidine were stirred together in 100 ml. ethanol at reflux for 2 hr. After cooling, the reaction mixture was filtered and the filtrate concentrated to give 12.5 g. solid material which was determined by nuclear magnetic resonance spectrum analysis to be a salt. The crude product was treated with dilute sodium hydroxide solution and the free base extracted into chloroform twice. The chloroform extracts were combined, washed with water, dried over magnesium sulfate, filtered, and concentrated to give 6.8 g. of off-white solid product. Recrystallization from isopropyl ether-isopropanol gave 3.7 g. (30.7%) white solid, m.p. 133.5°–135.5° C.

Analysis: Calculated for $C_{22}H_{23}N_3O_2$: C, 59.72; H, 9.61; N, 17.14. Found (sublimed sample): C, 59.43; H, 9.54; N, 17.16.

FORMULATION AND ADMINISTRATION

Useful compositions containing at least one of the compounds according to the invention in association with a pharmaceutical carrier or excipient may be prepared in accordance with conventional technology and procedures. Effective quantities of the pharmacologically active compounds may be administered to a living animal body for therapeutic purposes in a form suitable for oral or parenteral administration. For example, compositions for oral administration can be solid or liquid and can take the form of capsules, tablets, coated tablets and suspensions, such compositions comprising carriers or excipients conveniently used in the pharmaceutical art. Suitable tableting excipients include lactose, potato, and maize starches, talc, gelatin, and stearic, and silicic acids, magnesium stearate, and polyvinyl pyrrolidone.

For parenteral administration the carrier or excipient may be a sterile, parenterally acceptable liquid; e.g., water or a parenterally acceptable oil; e.g., arachis oil contained in ampules.

Advantageously, the compositions may be formulated as dosage units, each unit being adapted to supply a fixed dose of active ingredients. Tablets, capsules, coated tablets and ampules are examples of preferred dosage unit forms according to the invention. Each dosage unit adapted for oral administration can conveniently contain 5 to 500 mg. and preferably 20 to 200 mg. of the active ingredient, whereas each dosage unit adapted for intramuscular administration can conveniently contain 5 to 100 mg. and preferably 10 to 75 mg. of the active ingredient.

The following formulations are representative for all of the pharmacologically active compounds of the invention. Compounds that do not form salts are used in the formulations as the free base.

1. Capsules — Capsules of 5, 25 and 50 mg. of active ingredient per capsule are prepared. With the higher amounts of active ingredient, reduction may be made in the amount of lactose.

| Typical blend for encapsulation | Per Capsule, mg. |
|---|---|
| Active ingredient, as salt | 5.0 |
| Lactose | 296.7 |
| Starch | 129.0 |
| Magnesium stearate | 4.3 |

-continued

| Typical blend for encapsulation | Per Capsule, mg. |
|---|---|
| | Total 435.0 mg. |

2. Tablets — A typical formulation for a tablet containing 5 mg. of active ingredient per tablet follows. The formulation may be used for other strengths of active ingredient by adjustment of weight of dicalcium phosphate.

| | Per Tablet, mg. |
|---|---|
| 1. Active ingredient, as salt | 5.0 |
| 2. Corn starch | 13.6 |
| 3. Corn starch (paste) | 3.4 |
| 4. Lactose | 79.2 |
| 5. Dicalcium phosphate | 68.2 |
| 6. Calcium stearate | 0.9 |
| | Total 170.3 mg. |

Uniformly blend 1, 2, 4 and 5. Prepare 3 as a ten percent paste in water. Granulate the blend with starch paste and pass the wet mass through an eight-mesh screen. The wet granulation is dried and sized through a twelve-mesh screen. The dried granules are blended with the calcium stearate and compressed.

Additional tablet formulations preferably contain a higher dosage of the active ingredient and are as follows:

| 50 mg. Tablet | |
|---|---|
| Ingredients | Per Tablet, mg. |
| Active ingredient, as salt | 50.0 |
| Lactose | 90.0 |
| Milo starch | 20.0 |
| Corn starch | 38.0 |
| Calcium stearate | 2.0 |
| | Total 200.0 mg. |

Uniformly blend the active ingredient, lactose, starches, and dicalcium phosphate when present. The blend is then granulated using water as a granulating medium. The wet granules are passed through an eight-mesh screen and dried at 140°–160° Fahrenheit overnight. The dried granules are passed through a ten-mesh screen, blended with the proper amount of calcium stearate, and the lubricated granules then converted into tablets on a suitable tablet press.

| 3. Injectable - 2% sterile solution | Per cc. |
|---|---|
| Active ingredient, as salt | 20 mg. |
| Preservative, e.g., chlorobutanol | 0.5% weight/volume |
| Water for injection | q.s. |

Prepare solution, clarify by filtration, fill into vials, seal, and autoclave.

Various modifications in the compounds, compositions and methods of the invention will be apparent to one skilled in the art and may be made without departing from the spirit or scope thereof, and it is therefore to be understood that the invention is to be limited only by the scope of the appended claims.

We claim:

1. A pharmaceutical composition having hypotensive activity comprising (a) from 5 milligrams to 500 milligrams of a 1-substituted-3-aminoethoxypyrrolidine selected from those having the formula:

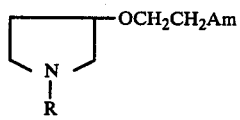

wherein;
R represents benzyl, 2-ethoxyphenoxylower-alkyl, 2-methoxy-4-acetylphenoxylower-alkyl, 4-fluorophenoxylower-alkyl, 2-methoxyphenoxylower-alkyl, or 2-piperidinoethyl, and
Am is morpholino, and
(b) a pharmaceutically acceptable carrier.

2. A pharmaceutical composition as defined in claim 1 wherein the 1-substituted-3-aminoethoxypyrrolidine is in the form of a pharmaceutically acceptable acid addition salt.

3. A pharmaceutical composition as defined in claim 1 wherein the compound is 1-[4-(p-fluorophenoxy)-butyl]-3-(2-morpholinoethoxy)pyrrolidine.

4. A pharmaceutical composition as defined in claim 1 wherein the compound is 1-(2-methoxyphenoxypropyl)-3-(2-morpholinoethoxy) pyrrolidine.

5. A method for producing a hypotensive effect in a host comprising administering to said host an effective amount of 1-substituted-3-aminoethoxypyrrolidine having the formula:

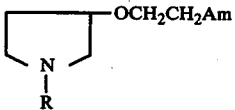

wherein;
R is benzyl, 2-ethoxyphenoxylower-alkyl, 2-methoxy-4-acetylphenoxylower-alkyl, 4-fluorophenoxy lower-alkyl, 2-methoxyphenoxylower-alkyl, or 2-piperidinoethyl,
Am is morpholino, and
the pharmaceutically acceptable acid addition salts thereof.

6. The method according to claim 5 wherein the 1-substituted-3-aminoethoxypyrrolidine is 1-[4-(p-fluorophenoxy)butyl]-3-(2-morpholinoethoxy)pyrrolidine.

7. The method according to claim 5 wherein the 1-substituted-3-aminoethoxypyrrolidine is 1-(2-methoxyphenoxypropyl)-3-(2-morpholinoethoxy)pyrrolidine.

8. 1-Benzyl-3-(2-morpholinoethoxy)pyrrolidine.

9. 1-Benzyl-3-(2-morpholinoethoxy)pyrrolidine dioxalate.

* * * * *